(12) United States Patent
Glass et al.

(10) Patent No.: US 9,434,974 B2
(45) Date of Patent: *Sep. 6, 2016

(54) INSTALLATION OF GENOMES OR PARTIAL GENOMES INTO CELLS OR CELL-LIKE SYSTEMS

(75) Inventors: John I. Glass, Germantown, MD (US); Lei Young, Gaithersburg, MD (US); Carole Lartigue, Gaithersburg, MD (US); Nacyra Assad-Garcia, Germantown, MD (US); Hamilton O. Smith, Reistertown, MD (US); Clyde A. Hutchison, La Jolla, CA (US); J. Craig Venter, Alexandria, VA (US)

(73) Assignee: Synthetic Genomics, Inc., San Diego, CA (US)

( * ) Notice: Subject to any disclaimer, the term of this patent is extended or adjusted under 35 U.S.C. 154(b) by 179 days.

This patent is subject to a terminal disclaimer.

(21) Appl. No.: 11/644,713

(22) Filed: Dec. 22, 2006

(65) Prior Publication Data
US 2007/0269862 A1    Nov. 22, 2007

Related U.S. Application Data

(60) Provisional application No. 60/752,965, filed on Dec. 23, 2005.

(51) Int. Cl.
| | |
|---|---|
| C12N 15/74 | (2006.01) |
| C12N 15/63 | (2006.01) |
| C12N 15/10 | (2006.01) |
| C12R 1/35 | (2006.01) |
| C12P 21/02 | (2006.01) |

(52) U.S. Cl.
CPC ............ *C12P 21/02* (2013.01); *C12N 2510/00* (2013.01)

(58) Field of Classification Search
None
See application file for complete search history.

(56) References Cited

U.S. PATENT DOCUMENTS 6,521,427 B1 * 2/2003 Evans ........................ 435/91.1

OTHER PUBLICATIONS

Ball et al. Synthetic biology, designs for life, Nature 448(7149):32-3, 2007.*
Lee et al., Development of a replicable oriC plasmid for Mycoplasma gallisepticum and Mycoplasma imitans, and gene disruption through homologous recombination in M. gallisepticum, Microbiology, 154(Pt 9):2571-80, 2008.*
Razin, Molecular biology and genetics of mycoplasmas (Mollicutes), Microbiol Rev. 49(4):419-55, 1985.*
Collas et al., Epigenetic reprogramming of nuclei using cell extracts, Stem Cell Rev. 2(4):309-17, 2006.*
Thaler et al., The cytoplasmic structure hypothesis for ribosome assembly, vertical inheritance, and phylogeny, Bioessays, 31(7):774-83, 2009.*
Sorek et al., Genome-wide experimental determination of barriers to horizontal gene transfer, Science 318(5855):1449-52, 2007.*
Groth et al., Chromatin Challenges during DNA Replication and Repair, Cell 128(4) 721-733, 2007.*
Gibson et al., "Creation of a bacterial cell controlled by a chemically synthesized genome", *Science*, 329(5987):52-56 (2010). Epub. May 20, 2010.
Lartigue et al., "Creating bacterial strains from genomes that have been cloned and engineered in yeast", *Science*, 325(5948):1693-1696 (2009). Epub Aug. 20, 2009.
"New Challenge to God" Part 3—Manipulating the Genes / 3 Forthcoming Birth of "Man-made Organisms", *Mainichi Newspaper*, Tokyo morning edition, p. 3, Apr. 18, 2001 (2 pages).
Huber et al., "A new phylum of Archaea represented by a nanosized hyperthermophilic symbiont", *Nature*, 417(6884):63-67 (2002).
Itaya et al., "Combining two genomes in one cell: stable cloning of the Synechocystis PCC6803 genome in the Bacillus subtilis 168 genome", *Proc. Natl. Acad. Sci. USA.*, 102(44):15971-15976 (2005). Epub. Oct. 18, 2005.
Kaneko et al., "DNA shuttling between plasmid vectors and a genome vector: systematic conversion and preservation of DNA libraries using the Bacillus subtilis genome (BGM) vector", *J. Mol. Biol.*, 349(5):1036-1044 (2005).
Nilsson et al., "Bacterial genome size reduction by experimental evolution", *Proc. Natl. Acad. Sci. USA.*, Aug. 23, 2005;102(34):12112-12116 (2005). Epub. Aug. 12, 2005.
Sugawara et al., "Constructive Approach Towards Origin of Life", *Biological Sciences in Space*, 20(1):10-14 (2006).
Check, Nature (2002) 420:350.
Hutchison et al., Science (1999) 286:2165-2169.
International Search Report and Written Opinion for PCT/US06/49231, mailed Jun. 17, 2008, 10 pages.
Lartigue et al., Science (2007) 317:632-638.
Smith et al., Proc. Natl. Acad. Sci. (2003) 100(26):15440-15445.
Noireaux et al., Physical Biology (2005) 2(3):P1-P8.
Supplementary Partial European Search Report for EP 06851502.2, mailed Sep. 23, 2009, 8 pages.

* cited by examiner

*Primary Examiner* — Gary Nickol
*Assistant Examiner* — Mary Lyons
(74) *Attorney, Agent, or Firm* — DLA Piper LLP (US)

(57) ABSTRACT

A method is provided for introducing a genome into a cell or cell-like system. The introduced genome may occur in nature, be manmade with or without automation, or may be a hybrid of naturally occurring and manmade materials. The genome is obtained outside of a cell with minimal damage. Materials such as a proteins, RNAs, polycations, nucleoid condensation proteins, or gene translation systems may accompany the genome. The genome is installed into a naturally occurring cell or into a manmade cell-like system. A cell-like system or synthetic cell resulting from the practice of the provided method may be designed and used to yield gene-expression products, such as desired proteins. By enabling the synthesis of cells or cell-like systems comprising a wide variety of genomes, accompanying materials and membrane types, the provided method makes possible a broader field of experimentation and bioengineering than has been available using prior art methods.

7 Claims, 3 Drawing Sheets

INSTALLATION OF GENOMES OR PARTIAL GENOMES INTO CELLS OR CELL-LIKE SYSTEMS

CROSS-REFERENCE TO RELATED APPLICATIONS

The present application claims benefit and priority from U.S. Provisional Patent Application Ser. No. 60/752,965 filed on Dec. 23, 2005, entitled, "Introduction of Genomes into Microorganisms," which is herein incorporated by reference.

This invention was made with government support (DOE grant no. DE-FG02-02ER63453). The government has certain rights in the invention.

BACKGROUND OF THE INVENTION

1. Field of the Invention

The present invention relates generally to cell biology, and more particularly to the synthesis of cells or cell-like systems.

2. Description of Related Art

Methods of altering cellular genomes and membranes are useful for testing hypotheses in the field of cell biology, as well as for the bioengineering of cell models, designer cells and organisms with tailored genomes. One recent approach to designing or altering cells is knocking out genes from bacterial cells to obtain cells with genomes that are smaller than the naturally occurring genome, which nonetheless remain capable of certain functions, such as reproduction. While such approaches afford some ability to learn about genomic function and design, approaches that enable fuller control over the contents of genomes, cell membranes and cell volumes will yield scientific and technological advances through superior experimental control and bioengineering capability.

What is desired is a method for synthesizing cells or cell-like systems so that a desired genome may be installed into a target cell, vesicle or other membrane-bound volume. An approach that allows the use of any genome, whether naturally occurring, manmade, or a hybrid of natural and manmade nucleic acid sequences, allows for the tailoring of the cellular and genomic environment, such as the inclusion or exclusion of materials on various scales (for example, small molecules, proteins, and/or ribosomes or nucleic acid translation and/or transcription systems), and allows for the design of the cellular membrane (again, drawing from naturally occurring membranes, manmade materials capable of forming aqueous compartments, or hybrids of such membranes and materials) will open vast horizons of genomic and cellular experimentation and design to basic research and biotechnological development.

SUMMARY OF THE INVENTION

A method is provided for installing a genome into a cell or cell-like system. The installed or introduced genome may occur in nature, be manmade with or without automation, or may be a hybrid of naturally occurring and manmade materials. The delicate genome is obtained outside of a cell with minimal damage. Materials that stabilize the genome or otherwise make it amenable to transfer into recipient cells or cell-like systems such as proteins, RNAs, polycations, or even systems as in a gene translation system, may accompany the genome. Some of the DNA nucleotides of the genome may be methylated or otherwise modified to make the genome more resemble a natural chromosome. The genome may be relaxed, supercoiled or even linearized if the normal configuration is circular. The genome is introduced into a naturally occurring cell or into a manmade cell-like system, such as a lipid vesicle or a ghost cell from which the naturally occurring genome has been suppressed or eliminated. A cell-like system or synthetic cell resulting from the practice of the provided method may be designed and used to yield gene-expression products, such as desired proteins, or to produce a novel manmade bacterial species whose designed genome makes it capable of extraordinary activities that are not performed by any natural cell, such as synthesizing peptides comprised of other than the standard 20 amino acids. By enabling the synthesis of cells or cell-like systems comprising a wide variety of genomes, accompanying materials and membrane types, the provided method makes possible a broader field of experimentation and bioengineering than has been available using prior art methods.

DETAILED DESCRIPTION OF THE INVENTION

Figure 1:
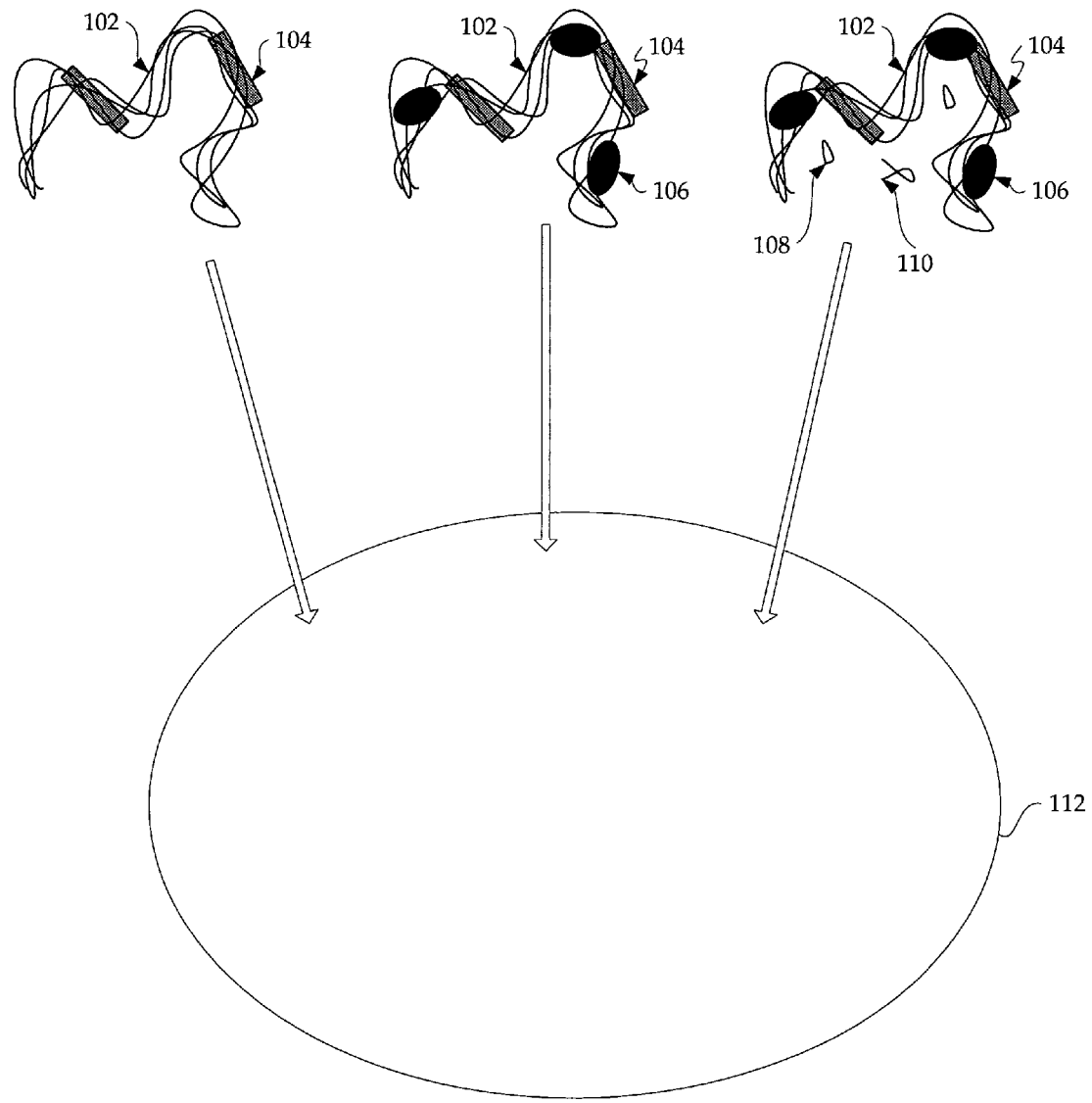
FIG. 1 is a diagram illustrating an exemplary method for installing a genome or partial genome into a cell or cell-like system.
Figure 2:
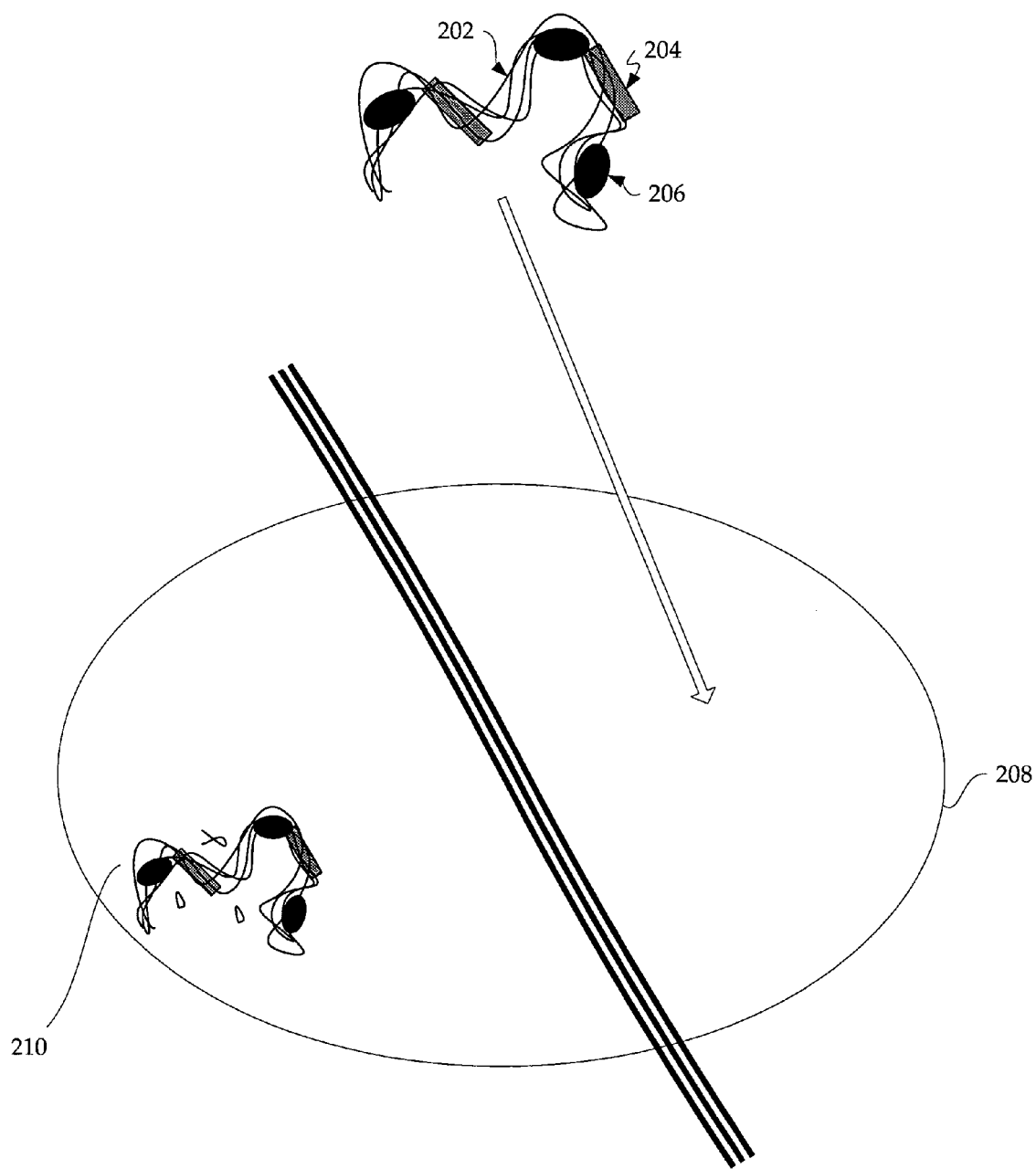
FIG. 2 is a diagram illustrating an exemplary method for installing a genome or partial genome comprising supercoiled DNA, scaffolding proteins and ribosomes (not to scale) into an *E. coli* cell that still contains its naturally occurring genome.

The ability to design a cell or cell-like system, including the genome, the membrane and the cytoplasm or membrane-bound aqueous volume, is particularly valuable in the fields of cell biology and biotechnology.

Embodiments of the present invention provide a method for synthesizing a cell or cell-like system. A "cell-like system" is a system that resembles a naturally occurring cell, but does not occur without human intervention. Cell-like systems include mammalian red blood cells (mammalian red blood cells do not naturally contain a genome) into which a genome or partial genome has been installed (or "introduced"), a "ghost cell" into which a genome has been introduced, an aqueous volume enclosed by a phospholipid bilayer (whether derived from a naturally occurring cell membrane, manmade, or a hybrid of naturally occurring and manmade components) into which a genome has been introduced, and an aqueous volume enclosed by a lipid vesicle into which a genome has been introduced. A ghost cell is a cell that naturally encloses a genome, but from which the naturally occurring genome is absent either as a result of genetic programming causing some cells to be genome-free or because the genome has been removed or inactivated. A partial genome comprises one or more chromosomes or chromosome fragments. For example, a partial genome may be any fraction of a naturally occurring genome, one or more fragments of one or more naturally occurring chromosomes, or one or more fragments of one or more naturally occurring chromosomes and one or more manmade nucleic acid sequences, one or more manmade nucleic acid sequences or fragments of manmade nucleic acid sequences, etc.

Ghost cells may be produced by any means, including but not limited to physical methods such ultraviolet and gamma irradiation, genetic methods involving minicells, and treatment with chemical compounds such as antibiotics and peroxides. In an exemplary embodiment, the naturally occurring genomes are removed from a cell of *Mycoplasma pneumoniae* and a cell of *Mycoplasma genitalium*, and the *M. genitalium* genome is introduced into the *M. pneumoniae* ghost cell. In some embodiments, ghost cells are produced from *M. alligatoris* and/or *M. capricolum*. Because both of these grow rapidly, their use yields results more quickly than that of *M. genitalium*, which takes three weeks to form a microscopic colony, or *M. pneumoniae*, which requires several days to form a colony.

A naturally occurring genome may be removed from a cell by any method, for example, by lysis and digestion. In an exemplary embodiment, about $10^{10}$ to about $10^{13}$ *Mycoplasma* cells grown in SP4 medium, in suspension or adherent to flasks, are washed with electroporation buffer comprising 8 mM HEPES with 272 mM sucrose at pH 7.4. The washed cells are added to 2.5 mL of the electroporation buffer at 4° C., triturated to break up any cell clumps, and pelleted by centrifugation at 4,575 g for 10 min at 4° C. The supernatant is decanted and the centrifuge tubes are inverted for a few minutes to minimize residual supernatant. Cells are resuspended in 100 µL of electroporation buffer plus 10 percent glycerol, and mixed with an equal amount of 2 percent low-melting-point agarose or agarose at about 56° C. The resulting cell suspension is cast in rectangular blocks while the agarose is still in a liquid state. Each block, or "plug," is then digested overnight at about 50° C. to 56° C. in 5 mL of proteinase K reaction cocktail (comprising 100 mM ethylenediaminetetraacetic acid (EDTA) at pH 8.0, 0.2 percent sodium deoxycholate, 1 percent sodium lauryl sarcosine, 2 percent sodium dodecyl sulfate, and 1 mg/mL proteinase K) per mL of plug. The plugs are then washed with 30 min of agitation four times in a wash buffer comprising 20 mM Tris buffer at pH 8.0 and 50 mM EDTA. The wash buffer for the second or third wash also comprises 1 mM phenylmethylsulfonyl fluoride. A synthetic genome may also be handled in this manner before introduction into a cell or cell-like system.

At this point the genomic DNA is relatively free of protein and other cytoplasmic components, and is suspended in agarose that protects it from shear and other forces that could fragment the genome during any subsequent, optional rounds of dialysis in 8 mM HEPES with 272 mM sucrose at pH 7.4 or other handling. The genomic DNA optionally can be subjected to pulsed-field gel electrophoresis to separate intact from fragmented genomes. Covalently closed circular genomes are relatively immobile in pulsed-field gel electrophoresis, while linear DNA molecules, RNA, and any remaining peptides electrophorese out of the agarose plugs. Thus, after pulsed-field gel electrophoresis, the plugs are highly enriched for covalently closed circular duplex DNA genomes. The genome-containing agarose plugs can be removed from the pulsed-field gels and processed for introduction into cells or cell-like systems. The excised plugs can be dialyzed in 10 mM Tris buffer at pH 7.5, 1 mM EDTA, 200 µM spermine (or other polyamine, such as polyethanolamine, or a nucleoid condensation protein such as Dps) and 25 mM NaCl at room temperature for 30 min to further compact the DNA through screening of its negative charges. The agarose may be digested with agarase, optionally after addition of 4 µg/mL low-molecular-weight poly-L-lysine, and commercial liposome-producing reagents may be added to yield a mixture useful for introducing genomes into cells or cell-like systems through transfection. A synthetic genome may also be handled in this manner before introduction into a cell or cell-like system.

An alternative example of obtaining a naturally occurring genome from a cell involves lysis and digestion in liquid rather than in agarose. After pelleting by centrifugation at 4,575 g for 10 min at 4° C., cells are lysed by adding sodium dodecyl sulfate at a final concentration of 1 percent. EDTA is added to a final concentration of 100 mM, RNase A is added at 10 U/mL and the mixture is incubated at 37° C. for 30 min, and then proteinase K is added at a concentration of about 20 to about 100 µg/mL and the mixture is incubated at 55° C. for about 3 to about 16 hours. The genomic DNA is then precipitated in 3 volumes of ethanol, the precipitation vessel is rolled gently so that the DNA adheres to its wall, the liquid is removed, and the DNA is washed several times with cold 70 percent ethanol and once with TE buffer (comprising 10 mM Tris-HCl at pH 7.4 and 1 mM EDTA). The ethanol/TE buffer is removed and the DNA is dried, and then resuspended in TE buffer plus 5 percent sucrose. A synthetic genome may also be handled in this manner with minimal DNA breakage before introduction into a cell or cell-like system.

The introduced genome may be any genome, such as a naturally occurring genome, a genome made with or without the aid of bioinformatics or other theoretical or computational methods, or a hybrid or chimaera of one or more naturally occurring and/or manmade genomes. For example, a cluster of genes occurring naturally in one or more organisms or organelles may be inserted into the naturally occurring genome of a microorganism or organelle, with or without the assistance of automated laboratory equipment. In some embodiments, the introduced genome is a minimal genome, such as the *E. coli* minimal genome or the *M. genitalium* minimal genome.

In an exemplary embodiment, the genome is prepared by assembling interchangeable nucleic acid "cassettes" by any pathway. A cassette is a nucleotide sequence of any length that is designed to comprise one or more genes or gene fragments, and optionally one or more regulatory, structural, or experimental sequences. The genes included in a cassette may be in any order (e.g., "shuffled" from a naturally occurring order), may occur multiple times, and may be incomplete or interrupted by other nucleic acid segments, such as genes or parts of genes. The nucleotide sequences included in a cassette may occur naturally, may be manmade with or without automated or computer assistance, or be a hybrid of one or more naturally occurring and one or more manmade sequences.

The introduced genome may comprise nucleic acid molecules of any kind. For example, the introduced genome may be composed of one or more stretches of one or more units of DNA (deoxyribonucleic acid), RNA (ribonucleic acid), or PNA (protein-nucleic acids), with or without modified or substituted nucleotides. Modified or substituted nucleotides include those that do not normally occur in biologically derived nucleic acid molecules, such as biotinylated nucleotides and nucleotides with altered ring, phosphate or sugar moieties. Nucleic acid molecules may comprise genes, as well as nonencoding regions such as binding sites for one or more proteins or other materials, or sites designed for attachment to substrate, or for any other purpose. The introduced nucleic acid molecules may be derived from any source, including cells of animals, plants or protists including archaebacteria, viruses, subcellular organelles and/or chemical synthesis. The introduced nucleic acid molecules may be the result of ab initio design of proteins or enzymes that do not occur naturally, such as aminoacyl tRNA synthetases for non-standard amino acids. The nucleic acid molecules optionally may be folded, supercoiled or otherwise compressed. In an exemplary embodiment the introduced nucleic acid molecules are double-stranded, but single-stranded nucleic acid molecules or nucleic acid molecules with other geometries are encompassed by the provided invention.

Introduction of a genome may be performed by any means. For example, a genome or other nucleic acid molecule may be enclosed in or complexed with either a liposome or a micelle, which may or may not also contain other matter such as supporting protein molecules, a system for transcription and translation, elemental ions, plastic or other particles and/or small molecular compounds. Then, the micelle or liposome containing or complexed with the genome may be contacted with a target host cell under circumstances that promote the incorporation of the vesicle contents into the cell. Other methods for installation of genomes into recipient cells or cell-like systems include physical approaches such as: optical tweezers, magnet assisted transfection in which genomes to be introduced are bound to magnetic nanobeads and then pulled into recipient cells by magnets, laser enhanced transformation, ballistic approaches in which the genomic DNA to be introduced is complexed with gold or tungsten nanoparticles and then blown at high velocity into the recipient cells, and electroporation; chemical methods such as: polyethylene glycol mediated methods, introduction via synthetic pores created in cells using cyclic peptides, calcium mediated precipitation of the DNA to be introduced onto the recipient cells with subsequent incorporation, and lithium acetate mediated precipitation of the DNA; and biological approaches such as: simple application of the DNA in agar plugs to the recipient cells followed by DNA uptake, fusogenic peptides, and induction of natural competency.

In an exemplary embodiment, *M. genitalium* chromosomes containing antibiotic resistance markers (such as tetM) are introduced into one or more *M. genitalium* or *M. pneumoniae* cells via lipofection (fusion of a liposome with a target cell to deliver the liposome contents into the target cell, described above). The one or more target cells are expected to lack the antibiotic resistance marker, thus remaining sensitive to tetracycline, to which the introduced genome is resistant. One day after lipofection, tetracycline may be added to the growth medium for one or more target cells, so that only the one or more target cells into which a genome has been introduced will grow. It may be necessary to disable the homologous recombination protein (RecA) of the recipient cells in order to avoid the antibiotic resistance marker recombining into the recipient cells.

In another exemplary embodiment, genomic DNA from *M. mycoides* is isolated via digestion in agarose as described above. One or more agarose plugs containing purified DNA are melted, mixed with polyethylinimine and cationic liposomes (e.g., LIPOFECTAMINE™ 2000 (Invitrogen)) and the genomic DNA is introduced into one or more *M. capricolum* cells via lipofection. In an exemplary embodiment, naked genomic DNA from *Mycoplasma mycoides* Large Colony is introduced into one or more *M. capricolum* cells using a polyethylene glycol mediated method.

The genome may be introduced into a cell or a cell-like system. Exemplary embodiments include introducing a genome into a living plant, animal, fungal, yeast, mitochondrion, chloroplast, or other cell or organelle, whether in vivo, in culture, or in other circumstances, introducing a genome into a cell from which the naturally occurring genome has been removed, and/or introducing a genome into a membrane-bound volume derived by any method, such as a red blood cell or a manmade lipid vesicle in aqueous solution. For example, a genome may be removed from an aquatic protist by lysis and digestion and introduced into a ghost cell by electroporation (see also U.S. Provisional Patent Application Ser. No. 60/752,965, cited above). Alternatively, the genome containing an antibiotic resistance gene or other selectable marker can be introduced into a living plant, animal, fungal, yeast, mitochondrion, chloroplast, or other cell or organelle so that transiently the cell or organelle contains both the introduced genome and its own genome. Subsequent cell or organelle division then segregates the introduced genome into a new daughter cell or organelle. That cell or organelle then takes on the phenotype programmed by its introduced genome.

In some embodiments a synthetic cell is produced, which may or may not be able to self-replicate. In an exemplary embodiment, a genome is introduced to a cell which already contains a naturally occurring genome, and the cell divides into two cells, one containing the naturally occurring genome, and another containing the introduced genome. Synthetic cells include the cell containing the introduced genome, as well as other microorganisms recognizable as engineered cells, for example, a cell from which the naturally occurring genome has been removed and into which a different genome has been introduced.

In an exemplary embodiment, one or more synthetic cells capable of replication contain a genome designed to express one or more particular gene products under certain conditions. For example, the naturally occurring genome may be removed from an *E. coli* cell, and a genome introduced that comprises a minimal genome for *E. coli* in a known growth medium and a cassette for expressing one or more therapeutic peptides, such as the insulin peptides. One or more of the altered, or synthetic, cells are cultured under conditions promoting their replication and expression of the therapeutic peptide, which then may be collected. One skilled in the art will be able readily to determine conditions appropriate for cell replication and expression of the one or more desired gene products.

FIG. 1 is a diagram illustrating an exemplary method for installing a genome or partial genome into a cell or cell-like system. A genome outside of a cell may comprise, for example, naked DNA (not shown), or one or more supercoiled nucleic acid molecules 102 with one or more scaffolding proteins 104, or one or more supercoiled nucleic acid molecules 102 with one or more scaffolding proteins 104 and one or more ribosomes 106 (not to scale), or one or more supercoiled nucleic acid molecules 102 with one or more scaffolding proteins 104, one or more ribosomes 106, and one or more accompanying small molecules 108 and one or more single-stranded nucleic acid molecules 110. One or more genomes may be introduced into a membrane bound aqueous volume 112, such as a lipid vesicle. In an exemplary embodiment, a genome comprising a minimal *M. genitalium* genome with cassettes added to produce a tomato protein and with marker nucleotides added is introduced in an agar plug to an *E. coli* cell that still contains its naturally occurring genome.

FIG. 2 is a diagram illustrating an exemplary method for installing a genome or partial genome including supercoiled DNA 202, scaffolding proteins 204 and ribosomes 206 (not to scale) into an *E. coli* cell 208 that still contains its naturally occurring genome 210. In this exemplary embodiment, the cell with two genomes divides along the hypothetical triple line in the diagram to produce a daughter cell with the naturally occurring *E. coli* genome 210, and a synthetic daughter cell with the introduced genome 202. The daughter cells may further self-replicate.

Figure 3:
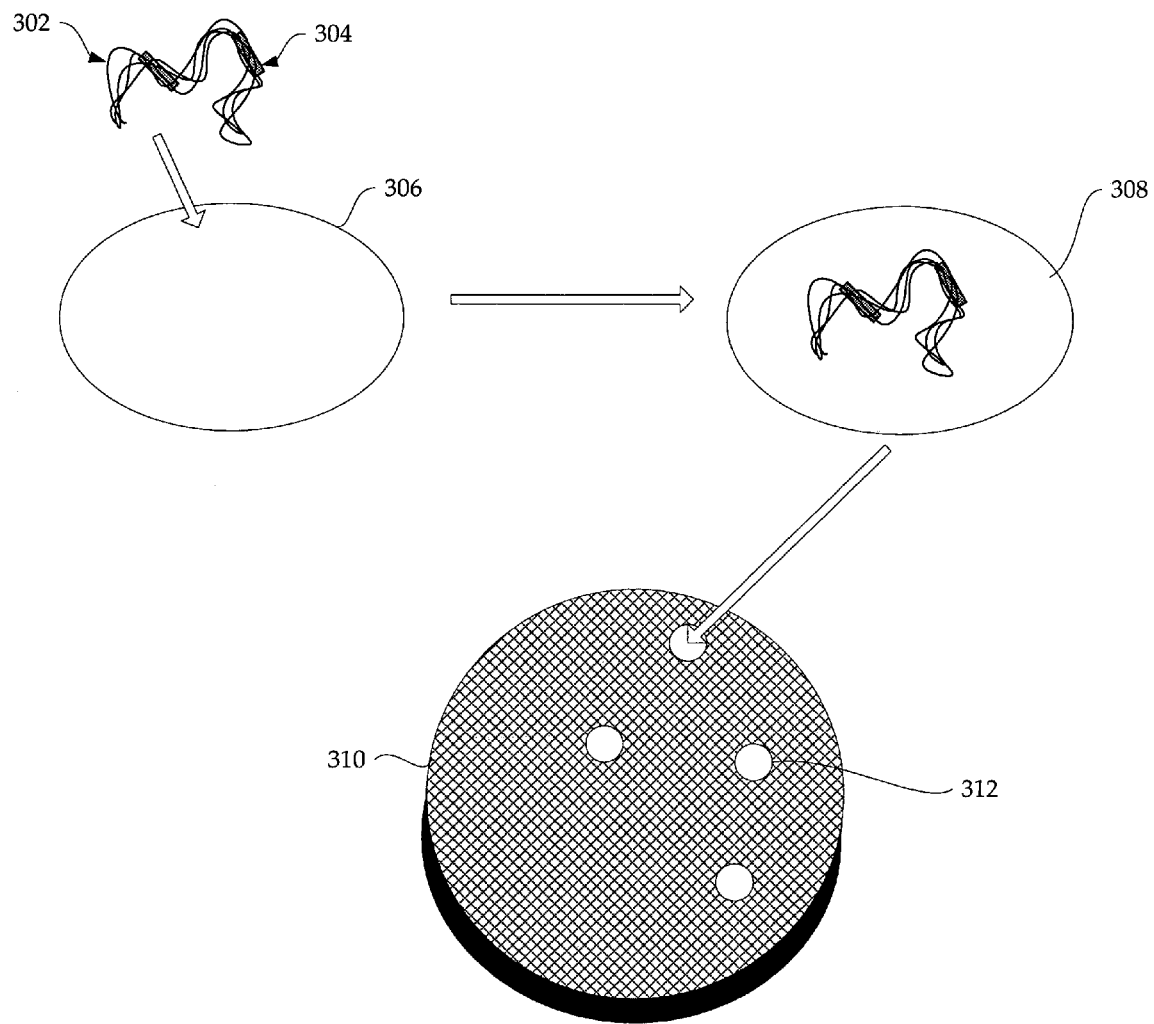
FIG. 3 is a diagram illustrating an exemplary method for producing a gene-expression product of interest using one or more synthetic cells.

FIG. 3 is a diagram illustrating an exemplary method for producing a gene-expression product of interest using one or more synthetic cells. In an exemplary embodiment, a synthetic genome 302 comprises a naturally occurring genome removed from a natural cell into which a manmade cassette coding for a desired protein has been spliced. The genome 302 is in the form of double-stranded, supercoiled DNA with scaffolding proteins 304. The genome 302 is introduced into a ghost cell 306 using, for example, optical tweezers. One or more such synthetic cells 308 with such genomes 302 are prepared and plated on a growth medium 310 that provides the synthetic cells 308 with the ability to self-replicate, forming one or more colonies 312 and expressing the desired protein.

While various embodiments have been described above, it should be understood that they have been presented by way of example only, and not limitation. For example, any other set of endonuclease reaction components that achieves the provided method may be used. Thus, the breadth and scope of a preferred embodiment should not be limited by any of the above-described exemplary embodiments.

What is claimed is:

1. A method for making a bacterial synthetic cell, the method comprising:

preparing a *Mycoplasma capricolum* recipient cell for installation of a bacterial genome;

isolating a genome from a *Mycoplasma mycoides* cell by suspending the isolated genome in an agarose suspension; and introducing the isolated genome into the *Mycoplasma capricolum* recipient cell by contacting the recipient cell with the genome.

wherein the genome of the *Mycoplasma capricolum* recipient cell is removed or inactivated to produce the recipient cell prior to, or after, introduction of the isolated genome by means of a physical, genetic or selective method or a combination thereof;

wherein the introduced genome is self-replicating; the introduced genome does not recombine with a genome of the recipient cell; and the recipient cell takes on the phenotype programmed by the introduced genome thereby producing a synthetic cell.

2. The method of claim 1, wherein the isolating step further comprises:

a) suspending the *Mycoplasma mycoides* cell in a melted agarose composition;

b) digesting the suspended *Mycoplasma mycoides* cell with a lysis mixture effective to lyse the cell, wherein the lysis mixture comprises a proteinase and a detergent;

c) washing the lysed *Mycoplasma mycoides* cell to form a suspension of the *Mycoplasma mycoides* genome in the melted agarose composition; and d) optionally separating linear DNA molecules, RNA, and peptides from the *Mycoplasma mycoides* genome.

3. The method of claim 1, wherein:

a) the isolating step further comprises optionally removing, digesting or melting the agarose in the genome suspension; and b) the introducing step further comprises combining the genome with the *Mycoplasma capricolum* recipient cell in the presence of cationic liposomes and the genomic DNA is introduced via lipofection.

4. The method of claim 1, wherein:

a) the isolating step further comprises optionally removing, digesting or melting the agarose in the genome suspension; and b) the introducing step further comprises combining the genome with the *Mycoplasma capricolum* recipient cell in the presence of polyethylene glycol.

5. The method of claim 1, wherein the *Mycoplasma capricolum* recipient cell comprises a ghost cell.

6. The method of claim 1, wherein the genome of the *Mycoplasma capricolum* recipient cell is removed prior to introducing the isolated bacterial genome.

7. The method of claim 1, wherein the genome of the *Mycoplasma capricolum* recipient cell is transiently present in the cell upon introduction of the isolated genome and is then removed by cell division to make a bacterial synthetic cell comprising the isolated genome.

* * * * *